United States Patent [19]

Kim et al.

[11] 4,306,085

[45] * Dec. 15, 1981

[54] HYDROFORMYLATION PROCESS USING RESIN-LIGAND-METAL CATALYST

[75] Inventors: Leo Kim; Timm E. Paxson, both of Houston; Sunny C. Tang, Katy, all of Tex.

[73] Assignee: Shell Oil Company, Houston, Tex.

[*] Notice: The portion of the term of this patent subsequent to Dec. 15, 1998, has been disclaimed.

[21] Appl. No.: 66,351

[22] Filed: Aug. 13, 1979

Related U.S. Application Data

[60] Continuation-in-part of Ser. No. 54,775, Jul. 5, 1979, abandoned, which is a division of Ser. No. 861,916, Dec. 19, 1977, Pat. No. 4,179,403.

[51] Int. Cl.$^3$ ..................... C07C 45/50; C07C 27/22
[52] U.S. Cl. .................................. 568/454; 568/882; 568/909; 252/431 R
[58] Field of Search ................ 260/604 HF; 568/909, 568/882, 454

[56] References Cited

U.S. PATENT DOCUMENTS

| | | | |
|---|---|---|---|
| 3,239,566 | 3/1966 | Slaugh et al. | 260/604 HF |
| 3,825,601 | 7/1974 | Rennick | 260/604 HF |
| 3,847,997 | 11/1974 | Allen | 260/604 HF |
| 3,929,898 | 12/1975 | Neinburg et al. | 260/604 HF |
| 3,954,883 | 5/1976 | Haag et al. | 260/604 HF |
| 3,994,978 | 11/1976 | Whitehurst | 260/604 HF |
| 3,998,864 | 12/1976 | Trevillyan | 260/604 HF |
| 4,098,727 | 7/1978 | Haag et al. | 260/604 HF |
| 4,144,191 | 3/1979 | Hartwell | 260/604 HF |

OTHER PUBLICATIONS

Pittman et al., "Chemtech", (1973), pp. 560-566.

*Primary Examiner*—Werren B. Lone

[57] ABSTRACT

The hydroformylation of olefinic hydrocarbons is effected by treating the hydrocarbon with hydrogen and carbon monoxide in the presence of a catalyst comprising an ion exchange resin and an organic linking compound having at least one resin-compatible moiety ionically bonded to said resin and further having at least one metal complexible moiety selected from the group consisting of cobalt, ruthenium, palladium, platinum and rhodium.

12 Claims, No Drawings

HYDROFORMYLATION PROCESS USING RESIN-LIGAND-METAL CATALYST

This application is a continuation-in-part of application Ser. No. 54,775, filed July 5, 1979, now abandoned whichis a divisional of application Ser. No. 861,916 filed Dec. 19, 1977, which issued as U.S. Pat. No. 4,179,403 on Dec. 18, 1979.

BACKGROUND OF THE INVENTION

1. Field of the Invention

This invention relates to a process for hydroformylating olefins to alcohols and/or aldehydes utilizing a catalyst comprising an ion exchange resin with a ligand ionically bonded thereto and with the ligand coordinately bonded to a transition element, particularly cobalt, ruthenium, palladium, platinum and rhodium.

2. Background

The use of heterogeneous catalysts over homogeneous catalysts has several advantages such as allowing the use of fixed beds, ease of separation of catalyst from the product and catalyst recovery and regeneration.

Traditionally, to produce heterogeneous catalysts from metals of the transition element series, these metals have been deposited on inert supports such as alumina or silica. More recently metal catalysts have been covalently attached to inert resin backbones by use of diphenylphosphine or other ligands which are attached directly to the polymer and coordinately bonded to the metal. Typical examples of this type are found in U.S. Pat. No. 3,998,864, issued Dec. 21, 1976, and in Pittman et al, *Chemtech*, p. 560–566, 1973.

In the composition utilized in the process of the invention, on the other hand, the metal is coordinately bound to a ligand and the ligand is ionically bound to an ion exchange resin. Some of the advantages of utilizing the materials in the process of the invention is that the materials are relatively simple to prepare using commercially available compounds, the preparations involve no exotic conditions, and often times may be carried out in an aqueous solvent system and the resins may be easily stripped of metal and ligands for isolation of the metal species and regeneration of the catalyst. The resin based catalysts utilized in the process of this invention have unique selectivity-reactivity properties when compared to their homogeneous analogues.

SUMMARY OF THE INVENTION

This invention provides a process for hydroformylating olefins which comprises treating said olefins with carbon monoxide and hydrogen at hydroformylation conditions in the presence of a novel heterogeneous catalyst comprising (a) an ion exchange resin, (b) a metal selected from the group consisting of cobalt, ruthenium, palladium, platinum and rhodium, and (c) a linking compound which has at least one moiety coordinately bound to the metal and further has at least one moiety which is ionically bonded to the ion exchange resins. The catalysts have unique selectivity-reactivity properties when compared to their homogeneous analogues and can easily be stripped of their expensive metal component and readily regenerated for future use.

DESCRIPTION OF THE PREFERRED EMBODIMENTS

Processes directed to the production of reaction mixtures comprising aldehydes and/or alcohols by the reaction of olefinic compounds with carbon monoxide and hydrogen at elevated temperatures and pressures in the presence of certain catalysts are well known in the art. The aldehydes and alcohols produced generally correspond to the compounds obtained by the addition of a carbonyl or carbinol group to an olefinically unsaturated carbon atom in the starting material with simultaneous saturation of the olefin bond. Isomerization of the olefin bond may take place to varying degrees under certain conditions with the consequent variation in the products obtained. These processes known in the industry, and referred to herein as hydroformylation, involve reactions which may be shown in the general case by the following equation:

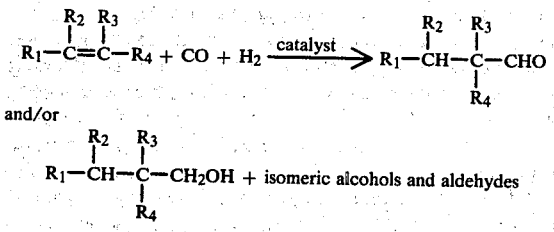

and/or $$R_1-CH-\underset{\underset{R_4}{|}}{\overset{\overset{R_2}{|}}{C}}-CH_2OH + \text{isomeric alcohols and aldehydes}$$

In the above equation, each R represents an organic radical, for example, hydrocarbyl, or a suitable atom such as hydrogen or a halogen. The above reaction is similarly applied to an olefinic linkage in a cycloaliphatic ring.

The hydroformylation of the unsaturated compound by treatment with carbon monoxide and hydrogen in the presence of the catalyst system of the present invention will be effected at hydroformylation conditions which include a temperature in the range of from about 40° to about 160° C., and preferably in a range of from about 60° to about 150° C. In addition, the reaction is also effected under superatmospheric pressures ranging from 1 up to about 500 atmospheres or more. The superatmospheric pressures are afforded by the introduction of gaseous carbon monoxide and hydrogen to the reaction zone or, if so desired, the pressure may be partially afforded by the carbon monoxide or hydrogen while the remaining pressure is afforded by a substantially inert gas such as nitrogen, helium or carbon dioxide although not necessarily with equivalent results.

Examples of suitable olefinic hydrocarbons which are utilized as a starting material in the hydroformylation process of this invention include, in particular, propylene, butene-1, butene-2, isobutene, pentene-1, pentene-2, 2-methylbutene-1, 2-methylbutene-2, hexene-1, 3-methypentene-1, 2-methylpentene-2, heptene-2, 2-methylhexene-2, 3-methylhexene-2, octene-1, octene-2, octene-3, heptene-1, nonene-1, decene-1, 3-methylheptene-1, 2-methylheptene-2, nonene-3, 3-methyloctene-2, decene-2, decene-5, decene-4, decene-3, 3,4-dimethyloctene-2, 4-ethyloctene-2, undecene-3, undecene-4, undecene-2, undecene-1, undecene-5, 4-methyldecene-2, 4,5-dimethylnonene-2, dodecene-1, dodecene-2, dodecene-3, dodecene-4, dodecene-5, tridecene-1, tridecene-2, tridecene-3, tetradecene-2, tetradecene-3, tetradecene-4, tetradecene-5, tetradecene-6, tetradecene-7, pentadecene-4, pentadecene-5, pentadecene-6, pentadecene-1, hexadecene-1, heptadecene-2, heptadecene-1, hexadecene-3, or mixtures of linear internal and terminal olefins such as internal olefins possessing carbon numbers between 11 and 14, 15 and 18, or 18 and 21, etc.

It is also contemplated within the scope of the process of the present invention that the hydroformylation may be effected in an inert organic medium as exemplified by n-pentane, n-hexane, n-heptane, n-octane, n-nonane, isooctane (2,2,4-trimethylpentane), cyclohexane, methylcyclohexane, benzene, toluene, m-xylene, mesitylene, etc.

It is understood that the aforementioned olefinic hydrocarbons and inert reaction mediums are only representative of the class of compounds which may be employed in the present hydroformylation invention and that the present invention is not necessarily limited thereto.

The desired products of the process of this invention, namely, alcohols and aldehydes, are utilized in the chemical industry in many ways. For example, alcohols are utilized in the synthesizing of other organic derivatives, as solvents, as an extraction medium, in dyes, synthetic drugs, synthetic rubbers, detergents, cleaning solutions, surface coatings, cosmetics, pharmaceuticals, in the preparation of esters, as a solvent for resin in coatings, in plasticizers, dyeing assistants, hydraulic fluids, detergent formulations and dehydrating agents. Aldehydes are utilized as perfumeries or precursors to perfumeries, or in the synthesis of primary alcohols. The non-linear alcohols and aldehydes are also utilized in the chemical industry in many other ways; for example, 2-methyl-1-butanol is utilized as a solvent in varnishes, lacquers and paint removers. Likewise, a general use of the non-linear alcohols and aldehydes is detergent formulations as exemplified by 2-butyl-1-heptanol.

The ratio of catalyst to the olefin to be hydroformylated is generally not critical and may vary widely within the scope of the invention. The ratio of catalyst to olefin charge may be varied to achieve a substantially homogeneous reaction mixture. Solvents are therefore not required. However, the use of solvents which are inert, or which do not interfere to any substantial degree with the desired hydroformylation reaction under the conditions employed, may be used within the scope of the invention. Saturated liquid hydrocarbons, for example, may be used as solvents in the process, as well as ketones, ethers, and the like. Molar ratios of catalyst to olefin between about 1:1000 and about 10:1 are found to be satisfactory; higher or lower catalyst to olefin ratios may, however, be used within the scope of the invention.

The ratio of hydrogen to carbon monoxide charged may vary widely within the scope of the invention. In general, a mole ratio of hydrogen to carbon monoxide of at least about 1 is employed. Suitable ratios of hydrogen to carbon monoxide comprise those within the range of from about 1 to about 10. Higher or lower ratios may, however, be employed within the scope of the invention. The ratio of hydrogen to carbon monoxide preferably employed will be governed to some extent by the nature of the reaction product desired. If conditions are selected that will result primarily in an aldehyde product, only one mole of hydrogen per mole of carbon monoxide enters into reaction with the olefin. When the alcohol is the desired product, two moles of hydrogen and one mole of carbon monoxide react with each mole of olefin. The minimum ratio of hydrogen to carbon monoxide employed will therefore generally be governed by the product desired. The use of ratios of hydrogen to carbon monoxide which are somewhat higher than those defined by these stoichiometrical values are generally preferred.

The ion exchange resins utilized to prepare the composition utilized in this invention are well known in the art and are readily available commercially. These are in the gel form or are macroporous and are either strongly acidic, weakly acidic, strongly basic, intermediate basic, weakly basic or mixed acid-base. The strong acid resins typically have base resins of cross-linked styrene, styrene divinyl benzene, phenol-formaldehydes, benzene-formaldehyde, having functional sulfonic or phosphonic acid groups attached thereto. Also suitable are the fluorinated alkyl sulfonic acid resins containing the -CFSO$_3$H group as, for example, the NAFION ® type resins supplied by E. I. DuPont de Nemours. The weak acid resins are those with carboxylic acid groups and are typically acrylic acid derivatives such as, for example, those resins prepared by the copolymerization of methacrylic acid and divinylbenzene. Another weak acid resin is the chelating type which is a styrene-divinylbenzene copolymer containing aminodiacetic acid functional groups which can serve as an anion exchanger at very low pH. The basic resins typically have base resins of cross-linked styrene, styrene-divinylbenzene, phenolformaldehydes, benzene-formaldehyde, epoxypolyamine, phenolicpolyamine having functional amine, either primary, secondary, tertiary or quaternary, or pyridinium groups attached thereto. Typical examples of suitable commercially supplied resins are given in Table I (reference: Bio-Rad Laboratories Catalogue, Chromatography, Electrophoresis, Immunochemistry and Membrane Filtration, Price List C, March 1977, p. 11).

TABLE I

| Type and Exchange Group | Bio-Rad | Dow Chem. Company "Dowex" | Diamond Shamrock "Duolite" | Rohm & Haas Co. "Amberlite" | Permutit Company (England) | Permutit Company (U.S.A.) |
|---|---|---|---|---|---|---|
| Anion exchange resins | | | | | | |
| Strongly Basic, polystyrene | AG 1-X1 | 1-X1 | | | DeAcidite FF | S-100 |
| $\phi$-CH$_2$N$^+$(CH$_3$)$_3$Cl$^-$ | AG 1-X2 | 1-X2 | | | (lightly | |
| | AG 1-X4 | 1-X4 | A-101D | IRA-401 | crosslinked) | |
| | AG 1-X8 | 1-X8 | | IRA-400 CG-400 | DeAcidite FF | |
| | AG 1-X10 | 1-X10 | | IRA-425 | | |
| | AG 21K | 21K | | IRA-402 | | |
| $\phi$-CH$_2$N$^+$(CH$_3$)$_2$(CH$_2$H$_4$OH) Cl$^-$ | AG 2-X4 | 2-X4 | A-102D | | | S-200 |

TABLE I-continued

| Type and Exchange Group | Bio-Rad | Dow Chem. Company "Dowex" | Diamond Shamrock "Duolite" | Rohm & Haas Co. "Amberlite" | Permutit Company (England) | Permutit Company (U.S.A.) |
|---|---|---|---|---|---|---|
| 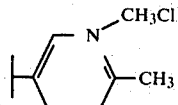 | AG 2-X8<br>AG 2-X10<br>Bio-Rex 9 | 2-X8 | | IRA-410 | | A-580 |
| Intermediate Base, epoxypolyamine<br>$R\!-\!N^+(CH_3)_2Cl^-$ and<br>$R\!-\!N^+(CH_3)_2(C_2H_4OH)\ Cl^-$ | Bio-Rex 5 | | A-30B | | F | S-310<br>S-380 |
| Weakly Basic, polystyrene or phenolic polyamine<br>$\phi\text{-}CH_2N^+(R)_2Cl^-$ | AG 3-X4A | WGR | A-6<br>A-7<br>A-4F | IR-45<br>IR-4B<br>IRA-68 | G | S-300<br>S-350 |
| Cation exchange resins | | | | | | |
| Strong Acidic, phenolic<br>$R\!-\!CH_2SO_3^-H^+$ | Bio-Rex 40 | | C-3 | | Zeocarb 215 | |
| Strong Acidic, polystyrene<br>$\phi\text{-}SO_3H^+$ | AG 50W-X1<br>AG 50W-X2<br>AG 50W-X4<br>AG 50W-X8<br>AG 50W-X10<br>AG 50W-X12<br>AG 50W-X16 | 50W-X1<br>50W-X2<br>50W-X4<br>50W-X8<br>50W-X10<br>50W-X12<br>50W-X16 | C-20<br>C-20X10<br>C-20X12 | IR-116<br>IR-118<br>IR-120<br>CG-120<br>IR-122<br>IR-124 | Zeocarb 225 (X4)<br>Zeocarb 225 | Permutit Q<br>Q-100<br>Q-110<br>Q-130 |
| Weakly Acidic, acrylic<br>$R\!-\!COO^-Na^+$ | Bio-Rex 70 | | CC-3 | IRC-50<br>CG-50 | Zeocarb 226 | Q-210 |
| Weakly Acidic, chelating resin, polystyrene<br>$\phi\text{-}CH_2N\!\!<\!\!\begin{array}{c}CH_2COO^-H^+\\CH_2COO^-H^+\end{array}$ | Chelex 100 | A-1 | | | | |
| Macroporous resins | | | | | | |
| Strong Base, polystyrene<br>$\phi\text{-}CH_2N^+(CH_3)_3Cl^-$ | AG MP-1 | MSA-1 | A-161 | IRA-900 | | |
| Strong Acid, polystyrene<br>$\phi\text{-}SO_3^-H^+$ | AG MP-50 | MSC-1 | C-25D | 200 | | |
| Mixed bed resins | | | | | | |
| $\phi\text{-}SO_3^-H^+$ &<br>$\phi\text{-}CH_2N^+(CH_3)_3OH^-$ | AG 501-X8 | | GPM-331 G | MB-1 | Bio-Demineralit | M-100 |

The preferred resin choice for the composition used in this invention will depend on the particular ionically bondable moiety utilized on the linking compound as well as on the particular use envisioned for the composition. For example, if the composition were used in liquid-phase catalysis, the composition and pH of the liquid would determine the preferred resin to be utilized.

The linking compound is hydrocarbyl, i.e., alkyl, aryl, or mixtures of aryl and alkyl components, which can be either cyclic or acyclic or mixtures thereof containing from 1 to about 100 carbon atoms, preferably from about 3 to about 80 carbon atoms and has at least two moieties containing an atom other than carbon.

At least one moiety is in the ionic or ionizable form and is compatible with the exchange group on the ion exchange resin, i.e., when the exchange group is acidic the resin-compatible ionic moiety on the linking compound is basic-derived and vice versa. The acidic-derived resin compatible ion moiety is derived from carboxylic acid ($RCO_2^-$), phosphonic acid ($RPO(OH)O^-$) phosphinic acid ($R_2POO^-$), sulfenic acid ($RSO^-$), sulfinic acid ($RSOO^-$), sulfonic acid ($RSO_2O^-$), boronic acid ($RB(OH)O^-$), boronous acid ($RBO^-$). The basic-derived resin compatible ion moiety is monohydrocarbyl ammonium ($RN^+H_3$), dihydrocarbyl ammonium ($R_2N^+H_2$), trihydrocarbyl ammonium ($R_3N^+H$), quarternary ammonium ($R_4N^+$), pyridinium ($RC_5H_4N^+R_1$), phosphonium ($R_4P^+$), arsonium ($R_4As^+$), and sulfonium ($R_3S^+$).

The linking compound may have more than one of the ionic moieties. It may be polyfunctional, for example, in carboxylate ion, in phosphonate ion, in sulfonate ion, in quaternary ammonium ion, in pyridinium and the like. The polyfunctional group may be the same or different.

At least one other moiety of the linking compound has an atom capable of complexing with metals from the transition element series, and consists of trivalent nitrogen, trivalent phosphorus, trivalent arsenic, trivalent bismuth, and trivalent antimony.

The three valances of the complexing atoms may be satisfied by any organic radical; saturated or unsaturated aliphatic, and/or saturated or unsaturated heterocyclic and/or aromatic radicals. These radicals may contain any functional group such as carbonyl, nitro, and hydroxy groups as well as saturated and unsaturated alkyl groups and the radical may be bonded to the complexing atom directly through a carbon-complexing atom linkage or through an electronegative atom such as oxygen or sulfur.

It is also suitable for a simple organic radical to satisfy more than one of the valence of the complexing atoms, thereby forming a heterocyclic compound with the trivalent complexing atom. For example, an alkylene radical may satisfy two of the valences thereby forming a cyclic compound. Another example would be the alkylene dioxy radical to form a cyclic compound where oxygen atoms link an alkylene radical to the complexing atom. In these two examples the third valence may be satisfied by any other organic radical.

The linking compound may have more than one of the metal-complexing moieties. It may be, for example, polydentate in phosphorus atom, e.g., it may be bi- or tridentate, having two or three phosphorus atoms. It may have mixed complexing atoms, e.g., a phosphorus and arsenic atom or two phosphorus atoms and one nitrogen atom, etc.

The trivalent nitrogen atom will be present as an amine, i.e., as a primary, secondary, tertiary, quaternary amine or as pyridine or cyanide. The trivalent phosphorus will be present as phosphine ($R_3P$), phosphinite ($ROPR_2$), phosphonite ($(RO)_2PR$) and phosphite ($RO_3P$). Correspondingly, trivalent arsenic will be available as arsine, arsinite, arsonite and arsenite, trivalent bismuth as bismuthine, bismuthinite, bismuthonite and bismuthite; and trivalent antimony as stibine, stibinite, stibonite and stibite. The preferred complexing atoms are phosphorus and nitrogen. The tertiary amines, phosphines, arsines and stibines and bismuthines have a marked tendency to form nonionic complexes with metals.

When the linking compound is polydentate in an ionizable heteroatom, it is understood that there will be a statistical distribution of the ionized atoms upon quaternization or protonation. For example, if one mole of a linking compound which contains 3 amine groups is protonated with 2 moles of HCl, then some of the molecules of the linking compound will have 3 quaternized amine groups, some will have 2 and some will have 1, but on the average there will be 2 quaternized amino groups per molecule. It is further understood from general principles of organic chemistry that unit charges resulting from quaternization and protonation can be distributed as partial charges over several heteroatoms in a linking compound molecule.

Thus the linking compound as reacted in the composition used in this invention will have at least one protonized or quaternized heteroatom and at least one heteroatom complexed with a transition element metal. Suitable linking compounds utilized in making the composition used in the invention include but are not limited to the following examples:

tris(dimethylamino)phosphine
tris(diethylamino)phosphine
tris(diisopropylamino)phosphine
tris(methylethylamino)phosphine
tris(p-dimethylaminophenyl)phosphine
tris(p-diethylaminophenyl)phosphine
tris(p-methylethylaminophenyl)phosphine
tris(o-dimethylaminophenyl)phosphine
tris(m-dimethylaminophenyl)phosphine
tris(dimethylaminoethyl)phosphine
tris(dimethylaminoethyl)phosphite
ethylbis(diphenylphosphinoethyl)amine.

Substitution of phosphinites, phosphonites, phosphites for the phosphine in the above compounds as well as arsines, arsinites, arsonites, arsenites, bismuthenes, bismuthinites, bismuthonites, bismuthites, stibines, stibinites, stibonites, stibites and amines produces linking compounds useful in preparing the composition used in this invention. Other suitable compounds are:

tris(4-N,N-dimethylaminophenyl)phosphine
2-(P,P-diphenylphosphino)benzoic acid
tris(beta-aminoethyl)amine
2-chloronicotinic acid, and 2-carboxypyridine
1,1-dimethyl-4-phenyl piperazinium salt
2,2'-alkylarsino-1,1'-diphenylamine
2-(P,P-dicyclohexylphosphino)benzoic acid
2-(P,P-dicyclohexylphosphino)propionic acid
beta-(dicyclohexylphosphino)propionic acid
1,4-(P,P-diphenylphosphino)benzene
2-diphenylphosphino-3-carboxy-2-butene
2-(P,P-diphenylphosphino)benzene sulfonic acid 2-amino-s-triazine
1-diphenylphosphino-2-diphenylphosphinoethane
tris-(beta-N,N-diarylaminoethyl)phosphite
tris(N,N-diarylamino)phosphine
bis-(beta-diphenylphosphinoethyl)ethylamine
3-(dialkylphosphino)benzene phosphonic acid.

Thus the organic linking compound is hydrocarbyl with at least one moiety capable of coordinate bonding and at least one moiety capable of ionic bonding. The primary limitation on the organic linking compound is a functional one, i.e., one moiety must be capable of coordinate bonding and the other moiety must be capable of ionic bonding. These moieties are well known to those skilled in the art.

The metals or metallic elements complexed with the linking compound are selected from the group consisting of cobalt, ruthenium, palladium, platinum and rhodium. As used herein the term "metal" refers to a "metal bonded coordinately" to the linking compound. Thus, as used herein, metal refers to a metallic compound rather than the metal which is found, for example, in a silver dollar.

The complexed metals can be in various oxidation states. See "Complexes of the Transition Metals with Phosphines, Arsines and Stibines", by G. Booth, Adv. Inorg. Nucl. Chem., 6, 1-69 (1964) for a comprehensive description of complexes. For example, the Booth reference cites the following oxidation states for metals complexed with phosphines.

TABLE II

| Metal | Oxidation State for Stable Phosphine Complexes |
|---|---|
| Ru | 0, 2, 3, 4 |
| Co | 1, 2, 3 |
| Rh | 0, 1, 3 |
| Pd | 0, 2 |
| Pt | 0, 2 |

Articles dealing with the complexing of amines with metals are "Inorganic Complexes", Jorgensen, C. K., Academic Press 1963, Chap. 4 and "Chemistry Coordination Compounds", Bailer (Ed.), Am. Chem. Soc. Monograph Series 131, 1956. The above references cite the following oxidation states for metals complexed with amines.

TABLE III

| Metal | Oxidation State of Stable Amine Complexes |
|---|---|
| Ru | 2, 3 |
| Co | 2, 3 |
| Rh | 3 |
| Pd | 2 |
| Pt | 0, 2, 4 |

The composition used in the invention may have more than one transition element metal present. The composition may also have the metal(s) co-complexed with other ligands in addition to the linking compound.

For example, from the above-noted Booth reference the metal complexed moiety of the composition could have the following form and still be within the scope of the invention, i.e., $M_Y$ $M_{Z'}$ $O_A$ $H_B$ $X_C$ $(CN^-)_D(CO)_E(NO)_F(Cp)_G(Py)_H(Acac)_I(AsR_3)_J(NR_3)_K(PR_3)_L(SnX_3^-)_M(GeX_3^-)_M(Carb)_N P_Q$ $M_Y$ = metal in oxidation state shown in Table II or Table III Y=0 to n mononuclear to polynuclear cluster $M_{Z'}$ = metal in oxidation state shown in Table II or Table III Z=0 to n mononuclear or mixed metal polynuclear cluster where n is an integer greater than 0 when Y>0 and Z>0

O = oxygen where A=0 to n

H = hydrogen where B=0 to n

X = halide F, Cl, Br, I; where C=0 to 5

$(CN^-)$ = cyanide where D=0 to 5 when y+z=1 or D=1 to n when y+x>1

(CO) = carbonyl where E=0 to 5 when y+z=1 or E=1 to n when y+z>1

(NO) = nitrosyl where F=0 to 5 when y+z=1 or E=1 to n when y+z>1

Cp = cyclopentadienyl where G=0 to 3 when w=z=1 or G=1 to n when y+z>1

Py = pyridine where H=0 to 5 when y+z=1 or H=1 to n when y+z>1

Acac = acetylacetonate where I=0 to 3 when y+z=1 or I=1 to n when y+z>1

$(AsR_3)$ = arsines, where R—H, alkyl or aryl and J=0 to 5 when y+z=1 or J=1 to n when y+z>1 the arsine also may be of the chelating type or contain mixed donating atoms e.g.

$(NR_3)$ = amines, where R=H, alkyl, or aryl and K=0 to 5 when y+z=1 or K=1 to n when y+z>1 as with arsines, a chelating or mixed donor chelating ligand may be employed.

$(PR_3)$ = phosphines where R=H, alkyl, or aryl, and L=0 to 5 when y+z=1 or L=1 to n when y+z>1 as with arsines, and amines, a chelating ligand may be employed $(SnX_3^-)$ or $(GeX_3^-)$ = trihalostannyl or trihalogermyl where X=F, Cl, Br, I and M=0 to 5 when y+z=1 or M=1 to n when y+z>1

(Carb) = carboxylate where N=0 to 5 when y+z=1 or N=1 to n when y+z>1

P = the bridging moiety/ligand between the metal and the resin support and Q=1 to n.

In general terms this invention is a process for hydroformylating olefins which comprises treating said olefin with carbon monoxide and hydrogen at hydroformylation conditions in the presence of a catalyst comprising an ion exchange resin, a metal or element selected from the group consisting of cobalt, ruthenium, palladium, platinum and rhodium, particularly cobalt and rhodium, and an organic linking compound which has at least one moiety which is ionically bonded to said ion exchange resin and further has at least one moiety which is coordinately bonded to said metal. In particular, the process will utilize, depending on the ion exchange resin, either a catalyst comprising:

(a) an ion exchange resin having a strongly acidic, weakly acidic, or mixed acid-base type functional group;

(b) a metal or element selected from the group consisting of cobalt, ruthenium, palladium, platinum and rhodium; and (c) an organic linking compound of from 1 to about 100 carbon atoms which has at least one moiety selected from the group consisting of monohydrocarbyl ammonium, dihydrocarbyl ammonium, trihydrocarbyl ammonium, quaternary ammonium, pyridinium and phosphonium which is ionically bonded to said ion exchange resin and further has at least one moiety which contains a heteroatom selected from the group consisting of trivalent nitrogen, trivalent phosphorus, trivalent arsenic, trivalent bismuth and trivalent antimony which is coordinately bonded to said element, or a catalyst comprising:

(a) an ion exchange resin having a basic-type functional group;

(b) a metal or element selected from the group consisting of cobalt, ruthenium, palladium, platinum and rhodium; and (c) an organic linking compound of from 1 to about 100 carbon atoms which has at least one moiety derived from the group consisting of carboxylic acid, phosphonic acid, phosphinic acid, sulfenic acid, sulfinic acid, sulfonic acid, boronic acid and boronous acid which is ionically bonded to said ion exchange resin and further has at least one moiety which contains a heteroatom selected from the group consisting of trivalent nitrogen, trivalent phosphorus, trivalent arsenic, trivalent bismuth and trivalent antimony which is coordinately bonded to said element.

The composition of this invention and preparation thereof is described by the following illustrative embodiments which are provided for illustration and are not construed as limiting the invention.

ILLUSTRATIVE EMBODIMENTS

The catalyst preparation procedures described below were carried out in nitrogen-filled dry boxes. The solvent benzene was purified by distillation over $CaH_2$, all other solvents were of reagent-grade and used as supplied. The metal complexes $[Rh(CO)_2Cl]_2$, $Rh(PPh_3)_3Cl$, $Rh(NO_3)_3$ in $H_2O$, $Co_2(CO)_8$, $Ru(PPh_3)_3Cl_2$, $PtCl_2(PPh_3)_2$, $[PtCl_2(PBu_3)]_2$, $Pd(C_6H_5CN)_2Cl_2$, $PdCl_2(PPh_3)_2$, $[Pd(allyl)Cl]_2$ and $Pd(OAc)_2$, and compounds $CH_3Br$, $SnCl_2 \cdot 2H_2O$, isonicotinic acid, and phosphines. $[(CH_3)_2N]_3P$, $[(CH_3)_2NC_6H_4]_3P$, $[(CH_3)_2NCH_2CH_2O]_3P$ were used as supplied. The quaternized aminophosphines were prepared by the reaction of 1 equivalent of $CH_3Br$ with an aminophosphine in toluene solution at room temperature. The quaternized aminophosphine precipitated readily from the toluene solution. The complex $Ru(CO)_3(PPh_3)_2$ (J. Chem. Soc. Dalton, 399 (1976)), $PtH(SnCl_3)(PPh_3)_2$ and $PtH(SnCl_3)(CO)(PPh_3)_2$ (J. Am. Chem. Soc. 97 3553 (1975)) were prepared as described in the references. The resins are indicated by (resin backbone)-(exchange group), e.g. a sulfonated styrene divinylbenzene resin would be (styrene-divinylbenzene)-$(SO_3^-)$, etc. Ph, $C_6H_5$ and $\phi$ are used as abbreviations for phenyl; —$\phi$— and $C_6H_4$ indicates p-substituted benzene moieties.

PREPARATION OF RESIN-LINKING COMPOUND MOIETY

Example 1

Preparation of sulfonated styrene-divinylbenzene resin/$[(CH_3)_2N]_3P$ compound.

The aminophosphine $[(CH_3)_2N]_3P$ (0.98 g, 60 mmol) was dissolved in 175 ml of acetone in a 250 ml round-bottomed flask. 5.0 Grams of Rohm and Haas XN1010H+ resin (acid form; macroreticular sulfonated styrene-divinylbenzene, 3.3 meq/g) which had previously been thoroughly washed with deionized water and dried was added to the flask. The mixture was then stirred magnetically from the side of the flask for 48 hours to prevent resin attrition. The resin was filtered by suction, washed with $3 \times 50$ ml of acetone, and dried in a vacuum oven (50° C.) overnight. Analysis showed the product as having the approximate formula (styrene-divinylbenzene)-$(SO_3^-)_{1.5}[([(CH_3)_2N]_3P)(H^+)_{1.5}]$.

Example 2

Preparation of sulfonated styrene-divinylbenzene resin/$[(CH_3)_2NC_6H_4]_3P$ compound.

The aminophosphine $[(CH_3)_2NC_6H_4]_3P$ (14.0 g, 35.8 mmol) was dissolved in 1000 ml warm benzene, cooled to room temperature, and filtered into a 2-l round-bottomed flask quickly. 10.0 G of XN1010H+ ion-exchange resin was added, and the mixture stirred magnetically on side of flask for 72 hours. The resin was then filtered, washed with benzene and vacuum dried in oven ($\sim 40°$ C.). Analysis showed the product as having the approximate formula (styrene-divinylbenzene)-$(SO_3^-)_{1.5}[([(CH_3)_2NC_6H_4]_3P)(H^+)_{1.5}]$.

Example 3

Preparation of sulfonated styrene-divinylbenzene resin/$[(CH_3)_2NCH_2CH_2O]_3P$ compound.

This material was prepared in a similar manner as in Example 1 except that 3.54 g (12.0 mmol) of the aminophosphine $[(CH_3)_2NCH_2CH_2O]_3P$, 10.0 g of XN1010H+ resin, and 300 ml of acetone were used. Analysis showed the product as having the approximate formula (styrene-divinylbenzene)-$(SO_3^-)_{1.5}[([(CH_3)_2NCH_2CH_2O]_3P)(H^+)_{1.5}]$.

Example 4

Preparation of sulfonated styrene-divinylbenzene resin/$[(\phi_2PCH_2CH_2)_2NCH_2CH_3]$ compound.

This material was prepared in a similar manner to Example 1 except that 2.82 g (6 mmol) of the aminophosphine $(\phi_2PCH_2CH_2)_2NCH_2CH_3$ and 200 ml of acetone was used. Analysis showed the product as having the approximate formula (styrene-divinylbenzene)-$(SO_3^-)_{1.5}[([(C_6H_5)_2PCH_2CH_2]_2NCH_2CH_3)(H^+)_{1.5}]$.

Example 5

Preparation of sulfonated styrene-divinylbenzene resin/methylquaternized $[(CH_3)_2N]_3P$ compound.

The quaternized aminophosphine $([(CH_3)_2N]_3P)(CH_3^+)Br^-$ (7.0 g wet) was dissolved in 350 ml of deionized water in a 500 ml round-bottomed flask. 10.0 G of XN1010Na ion-exchange resin (prepared by exhaustive ion-exchange of XN1010H+ with 10 l of 1 N NaCl or when the pH of the effluent was was neutral) was added. The mixture was side-stirred for 48 hours, filtered with suction, and the resin washed with $5 \times 100$ deionized $H_2O$, then vacuum dried in oven overnight (45° C.). Analysis showed the product as having the approximate formula (styrene-divinylbenzene)-$(SO_3^-)[([(CH_3)_2N]_3P)(CH_3^+)]$.

Example 6

Preparation of sulfonated styrene-divinyl benzene resin/methylquaternized $([(CH_3)_2NC_6H_4]_3P)$ compound.

This material was prepared in a similar manner as in Example 5 except that 10.4 (21.1 mmol) of the quaternized aminophosphine, 12.0 g of XN1010Na, and 1900 ml of an acetone/$H_2O$(12:7 v/v) solution were used. Analysis showed the product as having the approximate formula (styrene-divinylbenzene)-$(SO_3^-)[([(CH_3)_2NC_6H_4]_3P)(CH_3^+)]$.

Example 7

Preparation of sulfonated styrene-divinylbenzene resin/methylquaternized $[(CH_3)_2NCH_2CH_2O]_3P$ compound.

This material was prepared in a similar manner as in Example 5 except that 5.6 g (14.4 mmol) of the quaternized aminophosphine, 8.0 g of XN1010Na, and 400 ml of $H_2O$ were used. Analysis showed the product as having the approximate formula (styrene-divinylbenzene)-$(SO_3^-)[([(CH_3)_2NCH_2CH_2O]_3P)(CH_3^+)]$.

Example 8

Preparation of sulfonated styrene-divinylbenzene resin/methylquaternized $([(C_6H_5)_2PCH_2CH_2]_2NCH_2CH_3)]$ compound.

This material was prepared in a similar manner as in Example 5 except that 2.0 g (3.5 mmol) of the quaternized aminophosphine, 4.0 g of XN1010Na, and 200 ml of deionized water were used. Analysis showed the product as having the approximate formula (styrene-divinylbenzene)-$(SO_3^-)[([(C_6H_5)_2PCH_2CH_2]_2NCH_2CH_3)(CH_3^+)]$.

Example 9

Preparation of sulfonated styrene resin/$[(CH_3)_2NC_6H_4]_3P$ compound.

This material was prepared in a manner similar to Example 2 except that Dow MSC-1H resin (sulfonated polystyrene, macroreticular 1.6 meq/g) was used. Analysis showed the product as having the approximate formula (styrene)-$(SO_3^-)_{1.5}[([(CH_3)_2NC_6H_4]_3P)(H^+)_{1.5}]$.

Example 10

Preparation of sulfonated styrene resin/methylquaternized $([(CH_3)_2NC_6H_4]_3P)$ compound.

50 Grams of the hydrogen form of BioRad AG 50W-X1 (sulfonated polystyrene, 5.0 meq/g) was placed in a course fritted glass funnel which was then Na exchanged with 1 liter of 1 N NaCl by adding the salt solution in aliquots so it slowly ran through the resin. The resin was then washed in a similar manner with 2 liters of deionized water. This was followed by an acetone rinse and the resin was dried in a vacuum oven at about 40° C. for 2 days. A 5.0 g portion of the dried Na form of the resin was then added to 2 liters of an acetone-water solution (1:1 v/v) which contained the quaternized aminophosphine (2.0 g, 4.1 mmol) and stirred overnight under $N_2$. The material was then filtered and washed with an acetone solution, a water solution and then air-dried. Analysis showed the product as having the approximate formula (styrene)-$(SO_3^-)[([(CH_3)_2NC_6H_4]_3P)(CH_3^+)]$.

Example 11

Preparation of phosphonated styrene-divinylbenzene resin/methylquaternized $([(CH_3)_2NC_6H_4]_3P)$ compound.

This material was prepared in a manner similar to Example 10 except that 5.0 g of Bio-Rex 63 (microreticular gel), phosphonated, 6.6 meq/g) was used. Analysis showed the product as having the approximate formula (styrene-divinylbenzene)-$(PO_3^-)[([(CH_3)_2NC_6H_4]_3P)(CH_3^+)]$.

Example 12

Preparation of carboxylated acrylic resin/methylquaternized $([(CH_3)_2NC_6H_4]_3P)$.

This material was prepared in a manner similar to Example 10 except that 5.0 g of Bio-Rex 70 (acrylic polymer, carboxylic acid exchange group, 10.2 meq/g) was used. Analysis showed the product as having the approximate formula acrylic-$(CO_2^-)[([(CH_3)_2NC_6H_4]_3P)(CH_3^+)]$.

Example 13

Preparation of vinyl pyridinium resin/[o-$^-O_2CC_6H_4P(C_6H_5)_2$] compound.

A 10 g portion of Bio-Rex 9 (100-200 mesh, polymerized vinylpyridine, pyridinium type, 3.7 meq/g) was placed in a course grade fritted glass funnel and treated with 1 liter of 0.1 N HCl in the manner described in Example 10. The resin was then rinsed with 2 liters of deionized water, and finally with acetone. The resin was then dried for 2 days at about 40° C. in a vacuum oven.

A 5.0 g portion of resin was then added to about 500 ml of $H_2O$ in a round bottom flask. A 1.29 g (3.8 mmol) of diphenyl-(2-carboxyphenyl)phosphine was placed in a small flask of $H_2O$/acetone (5.0 g $H_2O$, 5.0 ml acetone) with 0.15 g of dissolved NaOH. After the phosphine was dissolved, the solution of phosphine was added to the solution which contained the resin. This was stirred overnight under an $N_2$ atmosphere. The material was filtered and washed with a 50-50 v/v mix of acetone/water and finally with acetone. Analysis showed the product having the approximate formula (ethylene)-(pyridinium$^+$) [o-$O_2CC_6H_4P(C_6H_5)_2^-$].

Example 14

Preparation of quaternary ammonium styrene-divinylbenzene resin/$(HO_2CC_5H_4N)$ compound.

To a solution of NaOH (1.5 g) in 150 ml of deionized $H_2O$ was added 4.6 g (38.4 mmol) of isonicotinic acid. To the resultant solution was added 6.0 g of Bio-Rad AG-1 (styrene-divinylbenzene microreticular anion-exchange resin, Cl-form, 20-50 mesh, 3.2 meq/g), side-stirred for 2 hours, and filtered by suction. The resin material was then washed with 3×50 ml of acetone, and dried in vacuum oven (45° C.). Analysis showed a product having the approximate formula (styrene-divinylbenzene)-$[CH_2N^+(CH_3)_3](^-O_2CC_5H_4N)$.

Example 15

Preparation of quaternary ammonium styrene resin/-$(HO_2CC_5H_4N)$.

This material was prepared in a similar manner as in Example 14 except that 5.9 g (48.0 mmol) of isonicotinic acid and 6.0 g of the Dow MSA-1 (macroreticular polystyrene base-quaternary exchange group, 4.0 meq/g) resin were used. Analysis showed a product having the approximate formula (styrene)-$[CH_2N^+(CH_3)_3]$-$(^-O_2CC_5H_4N)$.

PREPARATION OF RESIN-LINKING COMPOUND-METAL COMPLEX COMPOSITIONS

Example 16

Preparation of sulfonated styrene-divinylbenzene resin/$[(CH_3)_2N]_3P$/rhodium complex composition.

The rhodium dimer $[Rh(CO)_2Cl]_2$ (0.66 g., 1.7 mmol) was dissolved in 85 ml of benzene in a 100 ml round-bottomed flask, 1.5 g of the resin material prepared as described in Example 1 was added. The mixture was side-stirred magnetically for 1.5 hours, filtered by suction, and the resin washed with 3×50 ml of benzene. The resultant composition was dried under vacuum in an oven (45° C.) to give a material analyzed by neutron activation to have 8.4% w Rh and 2.9% w P. Analysis showed a composition having the approximate formula (styrene-divinylbenzene)-$(SO_3^-)_{1.5}[([(CH_3)_2N]_3P)(H^+)_{1.5}][Rh(CO)_2Cl]_{0.9}$.

Example 17

Preparation of sulfonated styrene-divinylbenzene resin/$[(CH_3)_2NC_6H_4]_3P$/rhodium complex composition.

A 2.0 g sample of the aminophosphine resin material prepared in example 2 was added to ca 25 mls of dry benzene in a 500 ml flask. To this mixture was added 0.12 gms (0.31 mmol) of $(Rh(CO)_2Cl)_2$. The entire reaction sequence was performed in a helium filled dry box.

The mixture was stirred for a 1.5 hour period and filtered to collect the composition which was washed with dry benzene and allowed to dry. The composition was stored in a tightly capped bottle in the dry box prior to use. Analysis showed a composition having the approximate formula (styrene-divinylbenzene)-$(SO_3^-)_{1.5}[([(CH_3)_2NC_6H_4]_3P)(H^+)_{1.5}][Rh(CO)_2Cl]_{0.4}$.

Example 18

Preparation of sulfonated styrene-divinylbenzene resin/$[(CH_3)_2NC_6H_4]_3P$/rhodium complex composition.

A 0.3 g sample of the aminophosphine/resin material prepared in Example 2 was treated in a similar manner as described in Example 17 except that 0.28 g (0.3 mmol) of $Rh(\phi_3P)_3Cl$ was used as the metal source. Analysis showed the composition having the approximate formula (styrene-divinylbenzene-$(SO_3^-)[([(CH_3)_2NC_6H_4]_3P)_x(H^+)_{1.5}](RhCl(\phi_3P)_{3-x})_{0.04}$ where x=1-3 because the aminophosphine can replace 1, 2 or 3 of the triphenylphosphine ligands on the metal complex.

Example 19

Preparation of sulfonated styrene-divinylbenzene resin/$[(CH_3)_2NCH_2CH_2O]_3P$/rhodium-complex composition.

This material was prepared in a similar manner as in Example 16 except that 0.61 g (1.6 mmol) of rhodium dimer $(Rh(CO)_2Cl)_2$ and the aminophosphine/resin material prepared as described in Example 3 were used. Analysis showed the composition having the approximate formula (styrene-divinylbenzene)-

$(SO_3{}^-)_{1.5}[([(CH_3)_2NCH_2CH_2O]_3P)(H^+)_{1.5}][Rh(CO)_2Cl]_{0.8}$.

Example 20

Preparation of sulfonated styrene-divinylbenzene resin/$[(\phi_2PCH_2CH_2)_2NCH_2CH_3]$/rhodium-complex composition.

This material was prepared in a similar manner as in Example 16 except that 0.48 g (1.23 mmol) or $[Rh(CO)_2Cl]_2$ and the aminophosphine resin material prepared as described in Example 4 were used. Analysis showed the composition as having the approximate formula (styrene-divinylbenzene)-$(SO_3{}^-)_{1.5}[([(C_6H_5)_2PCH_2CH_2]_2NCH_2CH_3)(H^+)_{1.5}][Rh(CO)_2Cl]_{0.3}$.

Example 21

Preparation of sulfonated styrene-divinylbenzene resin/methylquaternized $[(CH_3)_2N]_3P$/rhodium complex composition.

This material was prepared in a similar manner as in Example 16 except that 0.68 g (1.7 mmol) of $[Rh(CO)_2Cl]_2$ and 3.0 g of the aminophosphine resin material prepared as described in Example 5 were used. Analysis showed the composition as having the approximate formula (styrene-divinylbenzene)-$(SO_3{}^-)$ $[([(CH_3)_2N]_3P)(CH_3{}^+)][Rh(CO)_2Cl]_{1.4}$.

Example 22

Preparation of sulfonated styrene-divinylbenzene resin/methylquaternized $([(CH_3)_2NC_6H_4]_3P)$/rhodium-complex composition.

The aminophosphine/resin material prepared in Example 6 (2.0 gm) was treated with 0.17 gm (0.43 mmol) of $[Rh(CO)_2Cl]_2$ in benzene solution in a helium filled dry box in a manner similar to that described in Example 17. Analysis showed the composition as having the approximate formula (styrene-divinylbenzene)-$(SO_3{}^-)[([(CH_3)_2NC_6H_4]_3P)(CH_3{}^+)][Rh(CO)_2Cl]_{0.5}$.

Example 23

Preparation of styrene-divinylbenzene resin/methylquaternized $[(CH_3)_2NCH_2CH_2O]_3P$/rhodium complex composition.

This material was prepared in a similar manner as in Example 16 except that 0.08 g (0.21 mmol) of $[Rh(CO)_2Cl]_2$ and the aminophosphine resin material prepared as described in Example 7 were used. Analysis showed the composition as having the approximate formula (styrene-divinylbenzene)-$(SO_3{}^-)[([(CH_3)_2NCH_2CH_2O]_3P)(CH_3{}^+)][Rh(CO)_2Cl]_6$.

Example 24

Preparation of sulfonated styrene-divinylbenzene resin/methylquaternized $([(C_6H_5)_2PCH_2CH_2]_2NCH_2CH_3)$/rhodium-complex compound.

This material was prepared in a similar manner as in Example 16 except that 0.45 g (1.2 mmol) of the $[Rh(CO)_2Cl]_2$ rhodium and 1.2 g of the aminophosphine/resin material prepared as described in Example 8 were used. Analysis showed a composition having the approximate formula (styrene-divinylbenzene)-$(SO_3{}^-)$ $[([(C_6H_5)_2PCH_2CH_2]_2NCH_2CH_3)(CH_3{}^+)][Rh(CO)_2Cl]_{0.5}$.

Example 25

Preparation of sulfonated styrene resin/methylquaternized $([(CH_3)_2NC_6H_4]_3P)$/rhodium-complex composition.

This material was prepared in a manner similar to example 19 except that 0.26 g (0.68 mmol) of $[Rh(CO)_2Cl]_2$ and 1.2 g of the aminophosphine/resin material prepared as described in Example 10 were used. Analysis showed the composition as having the approximate formula (styrene)-$(SO_3{}^-)[([(CH_3)_2NC_6H_4]_3P)(CH_3{}^+)][Rh(CO)_2Cl]_{0.01}$.

Example 26

Preparation of phosphonated styrene-divinylbenzene resin/methylquaternized $([(CH_3)_2NC_6H_4]_3P)$/rhodium-complex composition.

In the manner described in Example 17, a 4.5-gm sample of the aminophosphine/resin material prepared in Example 11 was treated with 0.26 gms (0.68 mmol) of $[Rh(CO)_2Cl]_2$. Analysis showed a composition having the approximate formula (styrene-divinylbenzene)-$(PO_3{}^-)$ $[([(CH_3)_2NC_6H_4]_3P)(CH_3{}^+)][Rh(CO)_2Cl]_{0.1}$.

Example 27

Preparation of carboxylated acrylic resin/methylquaternized $([(CH_3)_2NC_6H_4]_3P)$/rhodium-complex composition.

In the manner described in Example 17, a 4.5-gm sample of the aminophosphine/resin material prepared in Example 12 was treated with 0.26 gms (0.68 mmol) of $[Rh(CO)_2Cl]_2$. Analysis showed the composition as having the approximate formula (acrylic)-$(CO_2{}^-)$ $[([(CH_3)_2NC_6H_4]_3P)(CH_3{}^+)][Rh(CO)_2Cl]_{0.01}$.

Example 28

Preparation of vinylpyridinium resin/$[o-{}^-O_2CC_6H_4P(C_6H_5)_2]$/rhodium-complex composition.

In the manner described in Example 17, a 2.4 gm sample of the phosphinobenzoic acid/resin material prepared in Example 13 was treated with 0.14 gms (0.34 mmol) of $[Rh(CO)_2Cl]_2$. Analysis showed the composition having the approximate formula (vinylpyridinium$^-$) $[o\text{-}{}^+O_2CC_6H_4P(C_6H_5)_2]$ $[Rh(CO)_2Cl]_{0.05}$.

Example 29

Preparation of sulfonated styrene-divinylbenzene resin/methylquaternized $([(CH_3)_2NC_6H_4]_3P)$/rhodium-complex composition.

In the manner described in Example 17, a 0.5-gm sample of the aminophosphine/resin material prepared in Example 6 was treated with 0.44 gm (0.48 mmol) $Rh(\phi_3P)_3Cl$. Analysis showed the composition as having the approximate formula (styrene-divinylbenzene)-$(SO_3{}^+)_x[([(CH_3)_2NC_6H_4]_3P)(CH_3{}^+)]_x$ $(RhCl[P(C_6H_5)_3]_{3-x})_{0.05}$ where x=1, 2 or 3.

Example 30

Preparation of sulfonate styrene-divinylbenzene resin/$](CH_3)_2N]_3P$/cobalt-complex composition.

This material was prepared in a similar manner as in Example 16 except that the cobalt dimer $Co_2(CO)_8$ (0.58 g, 1.7 mmol) was used instead of the rhodium dimer. Analysis showed the composition as having the approximate formula (styrene-divinylbenzene)-$(SO_3{}^-)_{1.5}$ $[([(CH_3)_2N]_3P)(H^+)_{1.5}][Co(CO)_4]_{0.5}$.

Example 31

Preparation of sulfonated styrene-divinylbenzene resin/](Ch$_3$)$_2$NC$_6$H$_4$]$_3$P/cobalt-complex composition.

This material was prepared in a similar manner as in Example 17 except that the complex dicobalt octacarbonyl (0.5 g, 1.45 mmol) and 2.0 g of the aminophosphine/resin material prepared as described in Example 2 were used. Analysis showed the compositions as having the approximate formula (styrene-divinylbenzene)-(SO$_3^-$)$_{1.5}$[[(CH$_3$)$_2$NC$_6$H$_4$]$_3$P)(H$^{30}$)$_{1.5}$][Co(CO)$_4$]$_{0.8}$.

Example 32

Preparation of sulfonated styrene-divinylbenzene resin/[(CH$_3$)$_2$NCH$_2$CH$_2$O]$_3$P/cobalt-complex composition.

This material was prepared in a similar manner as in Example 19 except that the complex Co$_2$(CO)$_8$ (0.54 g, 1.6 mmol) was used. Analysis showed the composition as having the approximate formula (styrene-divinylbenzene)-(SO$_3^-$)$_{1.5}$[[(CH$_3$)$_2$NCH$_2$CH$_2$O]$_3$P)(H$^+$)$_{1.5}$]-[Co(CO)$_4$]$_{0.3}$.

Example 33

Preparation of sulfonated styrene-divinylbenzene resin/[($\phi_2$PCH$_2$CH$_2$)$_2$NCH$_2$CH$_3$]/cobalt-complex composition.

This material was prepared in a similar manner as in Example 20 except that the complex Co$_2$(CO)$_8$ (0.42 g, 1.3 mmol) was used. Analysis showed the compositions as having the approximate formula (styrene-divinylbenzene)-(SO$_3^-$)$_{1.5}$[[(C$_6$H$_5$)$_2$PCH$_2$CH$_2$]$_2$NCH$_2$CH$_3$(H$^+$)$_{1.5}$]-[Co(CO)$_4$]$_{0.2}$.

Example 34

Preparation of sulfonated styrene-divinylbenzene resin/methylquaternized [(CH$_3$)$_2$N]$_3$P/cobalt-complex.

This material was prepared in a similar manner as in Example 21 except that the complex Co$_2$(CO)$_8$ (0.6 g, 1.7 mmol) and 24 g of the aminophosphine/resin material prepared as described in Example 5 were used. Analysis showed the composition as having the approximate formula (styrene-divinylbenzene)-(SO$_3^-$)[[(CH$_3$)$_2$N]$_3$P)(CH$_3^+$)][Co(CO)$_4$]$_{0.8}$.

Example 35

Preparation of sulfonated styrene-divinylbenzene resin/methylquaternized ([(CH$_3$)$_2$NC$_6$H$_4$]$_3$P)/cobalt-complex composition.

This material was prepared in a similar manner as in Example 22 except that the complex Co$_2$(CO)$_8$ (0.14 g, 0.4 mmol) and 20 g of the aminophosphine resin material prepared as described in Example 6 were used. Analysis showed the composition as having the approximate formula (styrene-divinylbenzene)-(SO$_3^-$)[[(CH$_3$)$_2$-NC$_6$H$_4$]$_3$P)(CH$_3^+$)][Co(CO)$_4$]$_{1.8}$.

EXAMPLE 36

Preparation of sulfonated styrene-divinylbenzene resin/methylquaternized [(CH$_3$)$_2$NCH$_2$CH$_2$O]$_3$P-/cobalt-complex composition.

This material was prepared in a similar manner as in Example 23 except that the complex Co$_2$(CO)$_8$ (0.07 g, 0.2 mmol) was used. Analysis showed the composition as having the approximate formula (styrene-divinylbenzene)-(SO$_3^-$)[[(CH$_3$)$_2$NCH$_2$CH$_2$O]$_3$P)(CH$_3^+$)][Co(CO)$_4$]$_2$.

EXAMPLE 37

Preparation of sulfonated styrene-divinylbenzene resin/methylquaternized ([(C$_6$H$_5$)$_2$PCH$_2$CH$_2$]$_2$NCH$_2$CH$_3$)/cobalt-complex composition.

This material was prepared in a similar manner as in Example 24 except that the complex Co$_2$(CO)$_8$ (0.4 g 1.2 mmol) was used. Analysis showed the composition of having the approximate formula (styrene-divinylbenzene)-(SO$_3^-$)[[(C$_6$H$_5$)$_2$PCH$_2$CH$_2$]$_2$NCH$_2$CH$_3$)(CH$_3^+$)][Co(CO)$_4$]$_{0.3}$.

EXAMPLE 38

Preparation of sulfonated styrene-divinylbenzene resin/[(CH$_3$)$_2$NC$_6$H$_4$]$_3$P/ruthenium-complex composition.

This material was prepared in a similar manner as in Example 17 except that the ruthenium complex Ru($\phi_3$P)$_3$Cl$_2$ (1.0 g, 1.1 mmol) and 1.0 g of aminophosphine/resin material prepared as described in Example 2 were used. Analysis showed the composition as having the approximate formula (styrene-divinylbenzene)-(SO$_3^-$)$_{1.5x}$[([(CH$_3$)$_2$NC$_6$H$_4$]$_3$P)$_x$(H$^+$)$_{1.5x}$](RuCl$_2$[P(C$_6$H$_5$)$_3$]$_{3-x}$)$_{0.2}$ where x=1, 2, or 3.

EXAMPLE 39

Preparation of sulfonated styrene-divinylbenzene resin/methylquaternized ([(CH$_3$)$_2$NC$_6$H$_4$]$_3$P)/ruthenium complex composition.

This material was prepared in a similar manner as in Example 22 except the ruthenium complex Ru($\phi_3$P)$_3$Cl$_2$ (0.19 g, 0.2 mmol) and 1.0 g of aminophosphine/resin material prepared as described in Example 6 were used. Analysis showed the composition as having the approximate formula (styrene-divinylbenzene)-(SO$_3^-$)$_x$[([(CH$_3$)$_2$-NC$_6$H$_4$]$_3$P)(CH$_3^+$)]$_x$ (RuCl$_2$[P(C$_6$H$_5$)$_3$]$_{3-x}$)$_{0.5}$ where=1, 2 or 3.

EXAMPLE 40

Preparation of sulfonated styrene-divinylbenzene resin/[(CH$_3$)$_2$N]$_3$P/ruthenium complex composition.

This material was prepared in a similar manner as in Example 16 except that the ruthenium complex Ru(CO)$_3$($\phi_3$P)$_2$ (1.1 g, 1.6 mmol) was used. Analysis showed the composition as having the approximate formula (styrene-divinylbenzene)-(SO$_3^-$)$_{1.5x}$[([(CH$_3$)$_2$N]$_3$P$_x$(H$^+$)$_{1.5x}$][Ru(CO)$_3$[P(C$_6$H$_5$)$_3$]$_{2-x}$)$_{0.05}$ where x=1 or 2.

EXAMPLE 41

Preparation of sulfonated styrene-divinylbenzene methylquaternized ([CH$_3$)$_2$NC$_6$H$_4$]$_3$P)/ruthenium-complex composition.

This material was prepared in a similar manner as in Example 39 except the ruthenium complex Ru(CO)$_3$($\phi_3$P)$_2$ (0.77 g, 1.1 mmol) was used. Analysis showed the composition as having the approximate formula (styrene-divinylbenzene)-(SO$_3^-$)$_x$[([(CH$_3$)$_2$NC$_6$H$_4$]$_3$P)(CH$_3^+$)]$_x$ (Ru(CO)$_3$[P(C$_6$H$_5$)$_3$]$_{2-x}$)$_{0.04}$ where x=1 or 2.

Example 42

Preparation of sulfonated styrene-divinylbenzene resin/[(CH$_3$)$_2$NCH$_2$CH$_2$O]$_3$P/ruthenium-complex composition.

This material was prepared in a similar manner as in Example 19 except that the ruthenium complex Ru(CO)$_3$($\phi_3$P)$_2$ (0.15 g, 0.21 mmol) was used. Analysis showed the composition as having the approximate formula (styrene-divinylbenzene)-(SO$_3{}^-$)$_{1.5x}$-[([(CH$_3$)$_2$NCH$_2$CH$_2$O]$_3$P)$_x$(H$^-$)$_{1.5x}$] (Ru(CO)$_3$[P(C$_6$H$_5$)$_3$]$_{2-x}$)$_{0.04}$ where x=1 or 2.

Example 43

Preparation of sulfonated styrene-divinylbenzene resin/[($\phi_2$PCH$_2$CH$_2$)$_2$NCH$_2$CH$_3$]/ruthenium-complex composition.

This material was prepared in a similar manner as in Example 20 except that the ruthenium complex Ru(CO)$_2$($\phi_3$P)$_2$ (0.87 g, 1.2 mmol) was used. Analysis showed the composition as having the approximate formula (styrene-divinylbenzene)-(SO$_3{}^-$)$_x$-[([(C$_6$H$_5$)$_2$PCH$_2$CH$_2$]$_2$NCH$_2$CH$_3$)(H$^-$)]$_x$ (Ru(CO)$_3$[P(C$_6$H$_5$)$_3$]$_{2-x}$)$_{0.04}$ where x=1 or 2.

Example 44

Preparation of sulfonated styrene-divinylbenzene resin/methylquaternized [(CH$_3$)$_2$N]$_3$P/ruthenium-complex composition.

This material was prepared in a similar manner in Example 21 except that the ruthenium complex Ru(CO)$_3$($\phi_3$P)$_2$ (1.23 g, 1.7 mmol) was used. Analysis showed the composition as having the approximate formula (styrene-divinylbenzene)-(SO$_3{}^-$)$_x$[([(CH$_3$)$_2$N]$_3$P)(CH$_3{}^+$)]$_x$ (Ru(CO)$_3$]P(C$_6$H$_5$)$_3$]$_{2-x}$)$_{0.04}$ where x=1 or 2.

Example 45

Preparation of sulfonated styrene-divinylbenzene resin/methylquaternized [(CH$_3$)$_2$NC$_6$H$_4$]$_3$P)/ruthenium-complex composition.

This material was prepared in a similar manner as in Example 22 except that the ruthenium complex Ru(CO)$_3$(P$\phi_3$)$_2$ (0.14 g, 0.2 mmol) and 1.0 g of the aminophosphine resin material prepared as described in Example 6 were used. Analysis showed the composition as having the approximate formula (styrene-divinylbenzene)-(SO$_3{}^-$)$_x$[([(CH$_3$)$_2$NC$_6$H$_4$]$_3$P)(CH$_3{}^+$)]$_x$ (Ru(CO)$_3$[P(C$_6$H$_5$)$_3$]$_{3-x}$)$_{0.01}$ where x=1 or 2.

Example 46

Preparation of sulfonated styrene-divinylbenzene resin/methylquaternized [(CH$_3$)$_2$NCH$_2$CH$_2$O]$_3$P/ruthenium-complex composition.

This material was prepared in a similar manner as in Example 23 except that the ruthenium complex Ru(CO)$_2$($\phi_3$P)$_2$ (0.15 g, 0.2 mmol) was used. Analysis showed the composition as having the approximate formula (styrene-divinylbenzene)-(SO$_3{}^-$)[([(CH$_3$)$_2$NCH$_2$CH$_2$O]$_3$P)(CH$_3{}^+$)]$_x$ (Ru(CO)$_3$[P(C$_6$H$_5$)$_3$)$_{2-x}$)$_{0.01}$ where x=1 or 2.

Example 47

Preparation of sulfonated styrene-divinylbenzene resin/methylquaternized ([(C$_6$H$_5$)$_2$PCH$_2$CH$_2$]$_2$NCH$_2$CH$_3$)/ruthenium-complex composition.

This material was prepared in a similar manner in Example 24 except that the ruthenium complex Ru(CO)$_2$($\phi_3$P)$_2$ (0.82 g., 1.2 mmol) was used. Analysis showed the composition as having the approximate formula (styrene-divinylbenzene)-(SO$_3{}^-$)$_x$[([(C$_6$H$_5$)$_2$PCH$_2$CH$_2$]$_2$NCH$_2$CH$_3$)(CH$_3{}^+$)]$_x$ (Ru(CO)$_3$[P(C$_6$H$_5$)$_3$]$_{2-x}$)$_{0.01}$ where x=1 or 2.

Example 48

Preparation of sulfonated styrene-divinylbenzene resin/[(CH$_3$)$_2$NC$_6$H$_4$]$_3$P/palladium-complex composition.

The aminophosphine/resin material (0.3 g) prepared in Example 2 was treated with 0.12 g (0.3 mmol) of Pd($\phi$CN)$_2$Cl$_2$ in a manner similar to that described in Example 17. Analysis showed the composition having the approximate formula (styrene-divinylbenzene)-(SO$_3{}^-$)$_{1.5x}$[([(CH$_3$)$_2$NC$_6$H$_4$]$_3$P)$_x$(H$^+$)$_{1.5x}$][Pd(C$_6$H$_5$CN)$_{2-x}$Cl$_2$]$_{0.5}$ where x=1 or 2.

Example 49

Preparation of sulfonated styrene-divinylbenzene resin/methylquaternized [(CH$_3$)$_2$NC$_6$H$_4$]$_3$P/palladium-complex composition.

The aminophosphine/resin material (0.5 g) prepared in Example 6 was treated with 0.18 g (0.48 mmol) of Pd($\phi$CN)$_2$Cl$_2$ in a manner similar to that described in Example 17. Analysis showed the composition as having the approximate formula (styrene-divinylbenzene)-(SO$_3{}^-$)$_x$[([(CH$_3$)$_2$NC$_6$H$_4$]$_3$P)-(CH$_3{}^+$)]$_x$[Pd(C$_6$H$_5$CN)$_{2-x}$Cl$_2$]$_{0.5}$ where x=1 or 2.

Example 50

Preparation of sulfonated styrene-divinylbenzene resin/[(CH$_3$)$_2$NC$_6$H$_4$]$_3$P/palladium-complex composition.

To a solution of 0.73 g (1.0 mmol) of PdCl$_2$($\phi_3$P)$_2$ in 70.0 ml CHCl$_3$ was added 2.0 g of the aminophosphine/resin material prepared as described in Example 2. The mixture was stirred for 1 hour, filtered, washed with CHCl$_3$, and dried under vacuum. The resultant composition was Soxhlet-extracted with methyl ethyl ketone for 4 hours, and dried in vacuum oven at approx. 40° C. Analysis showed the composition as having the approximate formula (styrene-divinylbenzene)-(SO$_3{}^-$)$_{1.5x}$[([(CH$_3$)$_2$NC$_6$H$_4$]$_3$P)$_x$(H$^+$)$_{1.5x}$](PdCl$_2$[P(C$_6$H$_5$)$_3$]$_{2-x}$)$_{0.2}$ where x=1 or 2.

Example 51

Preparation of sulfonated styrene-divinylbenzene resin/[(CH$_3$)$_2$NC$_6$H$_4$]$_3$P/palladium-tin-complex composition.

2.0 Grams of aminophosphine/resin material prepared as described in Example 50 (prior to the Soxhlet-extraction step) was added to a filtered solution of 1.2 g (5.2 mmol) of SnCl$_2$.2H$_2$O in 200 ml of acetone. The mixture was stirred on side for 1 hour, filtered, washed with acetone, vacuum dried, Soxhlet-extracted with methyl ethyl ketone for 4 hours, and dried in vacuum at 40° C. Analysis showed the composition as having the approximate formula (styrene-divinylbenzene)-(SO$_3{}^-$)$_{1.5x}$[([(CH$_3$)$_2$NC$_6$H$_4$]$_3$P)$_x$(H$^+$)$_{1.5x}$](SnCl$_2$)$_{0.2x}$(PdCl$_2$[P(C$_6$H$_5$)$_3$]$_{2-x}$)$_{0.2}$ where x=1 or 2.

Example 52

Preparation of sulfonated styrene divinylbenzene resin/](CH$_3$)$_2$NC$_6$H$_4$]$_3$P/palladium-complex composition.

The palladium dimer [Pd(allyl)Cl]$_2$ (1.36 g, 3.5 mmol was dissolved in 50 ml of toluene and stirred overnight with 5.0 g of aminophosphine/resin material prepared as described in Example 2. The resulting composition then filtered, washed with toluene, Soxhlet-extracted with toluene for 4 hours and dried under vacuum at 50° C. Analysis showed the composition as having the approximate formula (styrene-divinylbenzene)-$(SO_3^-)_{1.5x}[[(CH_3)_2NC_6H_4]_3P)_x(H^+)_{1.5x}][PdCl(C_3H_5)_{2-x}]_{0.2}$ where x=1 or 2.

Example 53

Preparation of quaternary ammonium styrene-divinylbenzene resin/$HO_2CC_5H_4N$)/palladium-complex composition.

To a toluene solution of palladium acetate (1.0 g 4.4 mmol) was added 6 g of isonicotinic acid/resin material prepared as described in Example 14; the mixture stirred on the side overnight, filtered, and the resulting composition Soxhlet-extracted with toluene for 5 hours. The material was then dried in vacuum oven overnight (45° C.). Analysis showed the composition as having the approximate formula (styrene-divinylbenzene)-$[CH_2N^-(CH_3)_3](^-O_2C-C_5H_4N)$ $[Pd(O_2CCH_3)_2]_{0.1}$.

Example 54

Preparation of quaternary ammonium styrene-divinylbenzene resin/($HO_2CC_5H_4N$)/palladium-complex composition.

The material was prepared in a similar manner as in Example 53 except the aminophosphine/resin material was that prepared as described in Example 15. Analysis showed the composition as having the approximate formula (styrene-divinylbenzene)-$[CH_2N^+(CH_3)_3](HO_2CC_5H_4N)$ $[PdO_2CCH_3)_2]_{0.1}$.

Example 55

Preparation of sulfonated styrene-divinylbenzene resin/$[(CH_3)_2NC_6H_4]_3P$/platinum-tin-complex composition.

To a 90 ml acetone solution of the platinum complex $PtH(SnCl_3)(\phi_3P)_2$ (1.2 g 1.2 mmol) was added 2.0 g of the aminophosphine/resin material prepared as described in Example 2, side-stirred magnetically for 1.5 hours, filtered, the resultant composition washed with acetone, and vacuum dried at 45° C. Analysis showed the composition as having the approximate formula (styrene-divinylbenzene)-$(SO_3^-)_{1.5x}$ $[([(CH_3)_2NC_6H_4]_3P)(H^+)]_{1.5x}(PtH(SnCl_3)[P(C_6H_5)_3]_{2-x})_{0.1}$ where x=1 or 2.

Example 56

Preparation of sulfonated styrene-divinylbenzene resin/methylquaternized $([(CH_3)_2NC_6H_4]_3P)$/platinum-tin-complex composition.

This material was prepared as in Example 55 except that 0.17 g (0.18 mmol) of the platinum complex and 1.0 g of the aminophosphine/resin material prepared as described in Example 6 were used. Analysis showed the composition as having the approximate formula (styrene-divinylbenzene)-$(SO_3^-)_x$ $[([(CH_3)_2NC_6H_4]_3P)(CH_3^+)]_x$ $(PtH(SnCl_3)[P(C_6H_5)_3]_{2-x})_{0.04}$ where x=1 or 2.

Example 57

Preparation of sulfonated styrene-divinylbenzene resin/methylquaternized $([(CH_3)_2NC_6H_4]_3P)$/platinum-tin-complex composition.

This material was prepared in a similar manner as in Example 55 except that the platinum complex $PtH(CO)(SnCl_3)(\phi_3P)_2$ was used instead and 200 ml of acetone was used. Analysis showed the composition as having the approximate formula (styrene-divinylbenzene)-$(SO_3^-)_{1.5x}[([(CH_3)_2NC_6H_4]_3P)$ $(CH_3^+)]_{1.5x}(PtH(SnCl_3)$ $[P(C_6H_5)_3]_{2-x})_{0.04}$ where x=1 or 2.

Example 58

Preparation of sulfonated styrene-divinylbenzene resin/$[(CH_3)_2NC_6H_4]_3P$/platinum-tin-complex compositions.

To a 50 ml benzene solution of $[PtCl_2(Bu_3P)]_2$ (1.2 g, 1.2 mmol) was added 2.0 g of aminophosphine/resin material prepared as described in Example 2, the mixture stirred on the side magnetically for 1.5 hours, and filtered. The resultant filtrate was passed through the resin material on the filter by gravity three times, filtered, and then washed with benzene, and vacuum dried. The resin material was then added to a 400 ml acetone solution of $SnCl_2 \cdot 2H_2O$ (2.5 g), side-stirred for 40 min., filtered, washed with acetone, and vacuum-dried. Analysis showed the composition as having the formula (styrene-divinylbenzene)-$(SO_3^-)_{1.5}[([(CH_3)_2NC_6H_4]_3$-$P)(H^+)_{1.5}](SnCl_2)_{0.2}[PtCl_2(n-C_4H_{10})_3P]_{0.2}$.

Example 59

Preparation of sulfonated styrene-divinylbenzene resin/methylquaternized $([(CH_3)_2NC_6H_4]_3P)$/platinum-tin-complex composition.

This material was prepared as described in Example 58 except that 0.33 (0.36 mmol) of $[PtCl_2(Bu_3P)]_2$ was used and the aminophosphine/resin material was then prepared as described in Example 6. Analysis showed the composition as having the formula (styrene-divinylbenzene)-$(SO_3^-)$ $[([(CH_3)_2NC_6H_4]_3P)(CH_3^+)]$-$(SnCl_2)_{0.2}(PtCl_2[(n-C_4H_{10})_3P])_{0.05}$.

PROCESSES UTILIZING COMPOSITIONS OF THE INVENTION

Example 60—Hydroformylation Process-Cobalt Catalyst

To a 300 ml ss Magnedrive autoclave was added 70 ml of benzene, 2.0 ml of n-decane (internal standard), 20.0 ml (160 mmol) of 1-hexene, and 0.5 g of the resin/ligand/cobalt catalysts listed in Table IV. The solution was deoxygenated with nitrogen. Synthesis gas ($CO/H_2$, 1:1, 1200 psig) was then charged to the reactor and the reactor is heated to 120° C. Gas chromatographic analysis revealed the following results shown in Table IV below:

TABLE IV

HYDROFORMYLATION WITH HETEROGENEOUS COBALT CATALYSTS

| 1-Hexene: | 20 ml (160 mmol) |
|---|---|
| Solvent: | Benzene |
| Total liquid volume: | 92 ml |
| Catalyst amount: | 0.5 g |
| Temperature: | 120° |
| Pressure: | 1200 psig initial |
| $H_2/CO$ (molar ratio): | 1.0 |
| Apparatus: | 300ml-SS autoclave |

| Catalyst | Time (hr) | Conv. (%) | Selectivities (%) $C_7$-ald | $C_7$-alc | hexane | $C_7$-alc normal: branch | Isomeric Ratio Et:2Me:normal | Avg (%) Material Balance | Rate (m/m/hr) | Co Leach (ppm/hr) |
|---|---|---|---|---|---|---|---|---|---|---|
| Example 30 | 16 | 24.1 | 99.3 | 0 | 0.7 | 2.40 | .07:.35:1 | | | |
| | 23 | 24.0 | 99.2 | 0 | 0.8 | 2.41 | .06:.35:1 | 104 | 7.0 | 1.0 |
| Example 31 | 2 | 13.0 | 97.5 | 0 | 0.7 | 2.66 | .08:.29:1 | | | |
| | 20 | 47.3 | 98.9 | 0.5 | 0.6 | 2.44 | .08:.33:1 | 98 | 23.5 | 1.3 |
| Example 32 | 21 | 8.8 | 99.3 | 0 | 0.7 | 2.64 | .05:.33:1 | 98 | 6.1 | 0.05 |
| Example 33 | 16 | 2.8 | 100 | 0 | 0 | 3.21 | .06:.25:1 | 97 | | |
| | 20 | 2.5 | 100 | 0 | 0 | 3.94 | .06:.28:1 | | 2.4 | 1.6 |
| Example 36 | 17 | 3.4 | 100 | 0 | 0 | 2.50 | .06:.34:1 | 115 | 2.4 | 0.01 |
| Example 37 | 20 | 11.6 | 100 | 0 | 0 | 2.87 | .06:.28:1 | 119 | 6.8 | 1.3 |

Example 61—Hydroformylation Process - Rhodium Catalyst

A. The hydroformylation process of Example 60 was repeated using the rhodium catalysts given in column 1 of Table V. The results are given in Table V below:

TABLE V

HYDROFORMYLATION OF HEXENE-1 WITH HETEROGENEOUS RHODIUM CATALYSTS

| 1-Hexene: | 20 ml (160 mmol) |
|---|---|
| Solvent: | Benzene |
| Total liquid volume: | 92 ml |
| Catalyst amount: | 0.5 g |
| Temperature: | 80° C. |
| Pressure: | 1200 psig initial |
| $H_2CO$ (molar ratio): | 1.0 |
| Apparatus: | 300ml-SS autoclave |

| Catalyst | Time (hr) | Conv. % | Selectivities (%) $C_7$-ald | $C_7$-alc | hexane | $C_7$-ald Normal: Branch | Isomeric Ratio 2Et:2Me:normal | Avg (%) Material Balance | Rate m/m/hr |
|---|---|---|---|---|---|---|---|---|---|
| Example 16 | 1 | 86.0 | 99.8 | 0 | 0.2 | 1.13 | .14:.74:1 | | |
| | 2 | 97.6 | 99.8 | 0 | 0.2 | 1.00 | .19:.82:1 | 96 | 340 |
| Example 19 | 1 | 68.7 | 99.8 | 0 | 0.2 | 1.06 | .16:.78:1 | | |
| | 2 | 98.0 | 99.8 | 0 | 0.2 | 0.97 | .19:.84:1 | 103 | 320 |
| Example 20 | 1 | 42.2 | 99.8 | 0 | 0.2 | 2.03 | 0:.49:1 | | |
| | 2 | 88.7 | 100 | 0 | 0 | 1.35 | .09:.65:1 | | |
| | 3 | 98.2 | 100 | 0 | 0 | 1.23 | .13:.68:1 | 96 | 390 |

B. Repeating the above hydroformylation experiment but using pentene feeds produced the results in Table VI below:

TABLE VI

HYDROFORMYLATION OF 1-2-PENTENE WITH HETEROGENEOUS RHODIUM CATALYST

| Pentene: | 4.5 g |
|---|---|
| Solvent: | n-octane 20 ml |
| Catalyst: | 0.125 g |
| Pressure: | ~1200 psig initial |
| $H_2/CO$ (molar ratio): | 1.0 |
| Apparatus: | 100 ml glass-lined autoclave |

| Catalyst | Olefin | Reaction Temp. °C. | Reaction Time hrs. | $C_6$ Aldehyde selec. % | Normal: Branch | Conversion % |
|---|---|---|---|---|---|---|
| Example 22 | 1-pentene | 90 | 1.5 | 99 | 1.4[a] | 89.6 |
| Example 22 | 2-pentene | 90 | 1.5 | 99 | 0.17[a] | 98.9 |

[a] No 3-methylpentanal observed.

C. Repeating the above hydroformylation experiment but using 1,5-cyclooctadiene feeds produced the results in Table VII below.

TABLE VII

HYDROFORMYLATION OF 1,5-CYCLOOCTADIENE WITH HETEROGENEOUS RHODIUM CATALYSTS

Total Press.

TABLE VII-continued
HYDROFORMYLATION OF 1,5-CYCLOOCTADIENE WITH HETEROGENEOUS RHODIUM CATALYSTS

| Catalyst | Time (hr) | (psig) Ave. | Conv. (%) | 1,3-COD | 4-CHOC$_8$= | x-CHOC$_8$= | CHOC$_8$ |
|---|---|---|---|---|---|---|---|
| Example 18 | 3.0 | 1200 | 15.1 | 45.8 | 54.2 | 0 | 0 |
|  | 4.0 |  | 16.8 | 42.2 | 57.7 | 0 | 0 |
|  | 5.0 |  | 30.5 | 36.9 | 63.1 | 0 | 0 |
|  | 6.0 |  | 31.6 | 27.8 | 72.2 | 0 | 0 |
| Example 29 | 2.0 | 1500 | 8.0 | 37.8 | 62.2 | 0 | 0 |
|  | 3.0 |  | 15.1 | 34.8 | 62.2 | 0 | 0 |
|  | 4.0 |  | 48.4 | 31.5 | 68.5 | 0 | 0 |
|  | 5.0 |  | 64.2 | 26.8 | 73.2 | 0 | 0 |
|  | 6.0 |  | 89.9 | 20.8 | 75.1 | 1.6 | <0.5 |
| Example 17 (first recycle) | 4.0 | 1350 | 0.8 | 46.1 | 53.9 | 0 | 0 |
|  | 5.0 |  | 9.9 | 45.1 | 54.9 | 0 | 0 |
|  | 6.0 |  | 16.8 | 42.1 | 57.9 | 0 | 0 |
| Example 22 (third recycle) | 0.5 | 1450 | 6.9 | 0 | 92.1 | 7.9 | 0 |
|  | 2.5 |  | 29.4 | 23.7 | 73.8 | 2.5 | 0 |
|  | 3.5 |  | 47.2 | 34.8 | 63.2 | 2.0 | trace |
|  | 5.5 |  | 54.2 | 34.0 | 64.1 | 1.9 | trace |
|  | 6.5 |  | 68.8 | 30.1 | 68.0 | 2.0 | trace |
| Example 25 | 4.0 | 1250 | 87.3 | 91.9 | 8.1 | 0 | 0 |
| Example 27 | 4.0 | 1140 | 13.4 | 92.5 | 6.3 | 1.2 | 0 |
| Example 26 | 4.0 | 1100 | 88.7 | 76.5 | 22.9 | trace | 0 |
| Example 28 | 1.0 | 1100 | 9.2 | 92.2 | 6.4 | 0 | 0 |
|  | 2.0 |  | 26.3 | 74.2 | 24.3 | 0 | 0 |
|  | 3.0 |  | 58.7 | 45.6 | 54.4 | 0 | 0 |
|  | 4.0 |  | 71.7 | 45.6 | 54.2 | 0.3 | 0 |

| Catalyst | Total to CHOC$_8$= | Mat. Bal (%) | Amt. Rh. Catalyst (mmol) | Leaching (ppm/hr) |
|---|---|---|---|---|
| Example 18 | 54.2 |  | 0.011 |  |
|  | 57.7 |  |  |  |
|  | 63.1 |  |  |  |
|  | 72.2 | 105 |  | 1.4 |
| Example 29 | 62.2 |  | 0.012 |  |
|  | 62.2 |  |  |  |
|  | 68.5 |  |  |  |
|  | 73.2 |  |  |  |
|  | 77.7 | 108 |  | 2.0 |
| Example 17 | 53.9 |  | 0.086 |  |
|  | 54.9 |  |  |  |
|  | 57.9 | — |  | 0.4 |
| Example 22 | 100 |  | 0.0204 |  |
|  | 76.3 |  |  |  |
|  | 65.2 |  |  |  |
|  | 66.0 |  |  |  |
|  | 70.0 | — |  | 0.6 |
| Example 25 | 8.1 | 105 | 0.001 | 0.1 |
| Example 27 | 7.5 | 99 | — | 0.2 |
| Example 26 | 22.9 | 113 | 0.0534 | 1.8 |
| Example 28 | 6.4 |  | 0.0131 |  |
|  | 24.3 |  |  |  |
|  | 54.4 |  |  |  |
|  | 54.5 | 111 |  | 0.5 |

300-ml, stirred autoclave (600 rpm)
T = 80–90° C.

EXAMPLE 62
Hydroformylation Process - Platinum Catalyst

The hydroformylation process of Example 60 was repeated using the platinum catalysts given in column 1 of Table VIII. The results are given in Table VIII below:

TABLE VIII

HYDROFORMYLATION WITH HETEROGENEOUS PLATINUM/TIN CATALYST

| | |
|---|---|
| 1-Hexene: | 20 ml (160 mmol) |
| Solvent: | Benzene |
| Total liquid volume: | 92 ml |
| Catalyst amount: | 1.0 g |
| Temperature: | 100° C. |
| Pressure: | 3000 psig initial |
| $H_2$/CO(molar ratio): | 1.0 |
| Apparatus: | 300ml-ss autoclave |

| Catalyst | Time (hr) | Conv. (%) | Selectivities (%) | | | $C_7$-ald linearity % | Pt leach Rate (ppm/hr) |
|---|---|---|---|---|---|---|---|
| | | | $C_7$-ald | $C_7$-alc | hexane | | |
| Example 57 | 20 | 1.4 | 90.1 | 0 | 0 | 89.7 | 0.02 |
| Example 55 | 6 | 4.6 | 88.0 | 5.5 | 2.6 | 92.2 | 0.32 |
| Example 58 | 17.3 | 25.4 | 97.8 | 0 | 1.2 | 86.1 | 2.4 |
| Example 59 | 23 | 11.8 | 97.9 | 0 | 0.1 | 80.4 | 0.03 |

What is claimed:

1. A process for hydroformylating olefins to the corresponding alcohols and/or aldehydes which comprises reacting said olefin with carbon monoxide and hydrogen at hydroformylation conditions including a temperature in the range of from about 40° to about 160° C. and a pressure in the range of from about 1 to about 500 atmospheres, in the presence of a catalyst consisting essentially of:
   (a) an ion exchange resin having a strongly acidic, weakly acidic, or mixed acid-base type functional group;
   (b) a metal selected from the group consisting of cobalt, ruthenium, palladium, platinum and rhodium; and
   (c) an organic linking compound of from 1 to about 100 carbon atoms which has at least one moiety selected from the group consisting of monohydrocarbyl ammonium, dihydrocarbyl ammonium, trihydrocarbyl ammonium, quaternary ammonium, pyridinium, phosphonium, arsonium and sulfonium which is ionically bonded to said ion exchange resin and further has at least one moiety which contains a heteroatom selected from the group consisting of trivalent nitrogen, trivalent phosphorus, trivalent arsenic, trivalent bismuth and trivalent antimony which is coordinately bonded to said metal.

2. The process of claim 1 where, in the catalyst, the ion exchange resin has a functional group selected from the group consisting of sulfonic acid, fluorinated alkyl sulfonic acid, phosphonic acid, carboxylic acid and aminocarboxylic acid, the ionically bonded moiety is selected from the group consisting of monohydrocarbyl ammonium, dihydrocarbyl ammonium, trihydrocarbyl ammonium, quaternary ammonium, pyridinium and phosphonium, and the coordinately bonded moiety contains a heteroatom selected from the group consisting of trivalent nitrogen and trivalent phosphorus.

3. The process of claim 2 where, in the catalyst, the ion exchange resin has a backbone selected from the group consisting of polymerized styrene, styrene-divinylbenzene, phenol-formaldehyde, benzene-formaldehyde, acrylic acid and methacrylic acid.

4. The process of claim 3 where, in the catalyst, the metal is selected from the group consisting of platinum, cobalt and rhodium.

5. The process of claim 4 where, in the catalyst, the metal is selected from the group consisting of platinum and rhodium.

6. The process of claim 5 where, in the catalyst, the metal is platinum.

7. A process for hydroformylating olefins to the corresponding alcohols and/or aldehydes which comprises reacting said olefin with carbon monoxide and hydrogen at hydroformylation conditions including a temperature in the range of from about 40° to about 160° C. and a pressure in the range of from about 1 to about 500 atmospheres, in the presence of a catalyst consisting essentially of:
   (a) an ion exchange resin having a basic-type functional group;
   (b) metal selected from the group consisting of cobalt, ruthenium, palladium, platinum and rhodium; and
   (c) an organic linking compound of from 1 to about 100 carbon atoms which has at least one moiety derived from the group consisting of carboxylic acid, phosphonic acid, phosphinic acid, sulfenic acid, sulfinic acid, sulfonic acid, boronic acid and boronous acid which is ionically bonded to said ion exchange resin and further has at least one moiety which contains a heteroatom selected from the group consisting of trivalent nitrogen, trivalent phosphorus, trivalent arsenic, trivalent bismuth and trivalent antimony which is coordinately bonded to said metal.

8. The process of claim 7 where, in the catalyst, the ion exchange resin has a functional group selected from the group consisting of primary, secondary, tertiary, quaternary amine and pyridinium and the ionically bonded moiety is selected from the group consisting of trivalent nitrogen and trivalent phosphorus.

9. The process of claim 8 where, in the catalyst, the ion exchange resin has a backbone selected from the group consisting of polymerized styrene, styrene-divinylbenzene, phenol-formaldehyde, benzene-formaldehyde, epoxypolyamine and phenolic-polyamine.

10. The process of claim 9 where, in the catalyst, the metal is selected from the group consisting of platinum, cobalt and rhodium.

11. The process of claim 10 where, in the catalyst, the metal is selected from the group consisting of platinum and rhodium.

12. The process of claim 11 where, in the catalyst, the metal is platinum.

* * * * *